(12) United States Patent
Weltmann et al.

(10) Patent No.: US 9,663,754 B2
(45) Date of Patent: May 30, 2017

(54) ATMOSPHEREIC PRESSURE PLASMA JET FOR DELIVERING ACTIVE SUBSTANCES ENCAPSULATED IN NANOPARTICLES OR MICROPARTICLES TO TISSUE

(75) Inventors: Klaus-Dieter Weltmann, Binz (DE); Thomas Von Woedtke, Sundhagen (DE); Olaf Lademann, Rostock (DE)

(73) Assignee: LEIBNIZ-INSTITUT FUER PLASMAFORSCHUN UND TECHNOLOGIE E.V, Greifswald (DE)

( * ) Notice: Subject to any disclaimer, the term of this patent is extended or adjusted under 35 U.S.C. 154(b) by 0 days.

(21) Appl. No.: 13/389,938

(22) PCT Filed: Aug. 8, 2010

(86) PCT No.: PCT/EP2010/061528
§ 371 (c)(1),
(2), (4) Date: Jul. 19, 2012

(87) PCT Pub. No.: WO2011/018423
PCT Pub. Date: Feb. 17, 2011

(65) Prior Publication Data
US 2012/0288934 A1 Nov. 15, 2012

(30) Foreign Application Priority Data
Aug. 11, 2009 (DE) .......................... 10 2009 028 462

(51) Int. Cl.
*A61N 1/04* (2006.01)
*A61L 2/00* (2006.01)
(Continued)

(52) U.S. Cl.
CPC ........... *C12M 35/02* (2013.01); *A61B 18/042* (2013.01); *A61L 2/14* (2013.01); *H05H 1/2406* (2013.01);
(Continued)

(58) Field of Classification Search
CPC .... A61N 1/0424; A61N 1/327; A61N 1/0412; C12M 35/02; A61L 2/0011; A61L 2/14
(Continued)

(56) References Cited

U.S. PATENT DOCUMENTS 8,894,644 B2 * 11/2014 Stieber et al. .................. 606/41
2004/0053873 A1 * 3/2004 Barman et al. ................. 514/44
(Continued)

FOREIGN PATENT DOCUMENTS

| EP | 1 765 044 | 3/2007 |
|---|---|---|
| EP | 2 160 081 | 3/2010 |
| WO | 2009 060213 | 5/2009 |

OTHER PUBLICATIONS

Stoffels E eta l. Cold Atmospheric Plasma: Charged Species and Their Interactions with Cells and Tissues, IEEE Trans Plasma Sci, 36: 1441-1457, 2008.*
(Continued)

*Primary Examiner* — Kami A Bosworth
*Assistant Examiner* — Matthew A Engel
(74) *Attorney, Agent, or Firm* — Soroker Agmon Nordman

(57) ABSTRACT

A device for treating living cells by plasmaporation contains, in addition to devices for generating plasma and generating a field, devices for mixing and transporting active substances, predominantly in the form of nano and microparticles, for affecting the metabolism of the cells.

**

(51) Int. Cl.
  *C12M 1/42* (2006.01)
  *A61B 18/04* (2006.01)
  *A61L 2/14* (2006.01)
  *H05H 1/42* (2006.01)
  *H05H 1/24* (2006.01)
  *A61B 18/00* (2006.01)

(52) U.S. Cl.
  CPC ..... *H05H 1/42* (2013.01); *A61B 2018/00613* (2013.01); *H05H 2001/245* (2013.01); *H05H 2001/2462* (2013.01); *H05H 2245/122* (2013.01)

(58) Field of Classification Search
  USPC .............. 435/173.6, 283.1; 99/451; 426/237; 604/20, 24
  See application file for complete search history.

(56) References Cited

U.S. PATENT DOCUMENTS

| | | | |
|---|---|---|---|
| 2004/0110297 A1* | 6/2004 | Miyoshi ................. | C12M 35/02 435/459 |
| 2007/0029500 A1* | 2/2007 | Coulombe et al. ....... | 250/423 F |
| 2008/0118941 A1* | 5/2008 | Chen et al. ..................... | 435/29 |
| 2008/0237484 A1 | 10/2008 | Morfill et al. | |
| 2009/0004717 A1* | 1/2009 | Jaroszeski et al. ........ | 435/173.6 |
| 2010/0296977 A1 | 11/2010 | Hancock | |
| 2011/0112528 A1* | 5/2011 | Stieber .................. | A61L 2/0011 606/41 |
| 2013/0068732 A1* | 3/2013 | Watson et al. ............. | 219/121.5 |
| 2014/0188071 A1* | 7/2014 | Jacofsky et al. .............. | 604/501 |

OTHER PUBLICATIONS

Stoffels et al. Cold Atmospheric Plasma: Charged Species and Their Interactions with Cells and Tissus. IEEE Transactions on Plasma Science, vol. 36, 2008.*

Fridman et al. (Comparison of Direct and Indirect Effects of Non-Thermal Atmospheric-Pressure Plasma on Bacteria, Plasma Processes and Polymers, vol. 4, Issue 4, May 22, 2007).*

Sesutu et al., Plasma enhanced chemical vapor depositions to encapsulate crystals in thin polymeric films: a new approach to controlling drug release rates. International Journal of Pharmaceutics 288 (2005) 253-261.*

Ogawa et al., An epoch-making application of discharge plasma phenomenon to gene-transfer . Biotech. Bioeng. (2005) 92(7):865-870.*

Wang, S., et al., "Discharge comparison of nonequilibrium atmospheric pressure Ar/$O_2$ and He/$O_2$ plasma jets," Applied Physics Letters, vol. 83, No. 16, XP-002617380, pp. 3272-3274, (Oct. 20, 2003).

Fridman, G., et al., "Applied Plasma Medicine," Plasma Processes and Polymers, vol. 5, No. 6, XP-002617381, pp. 503-533, (Aug. 2008).

International Search Report Issued Mar. 15, 2011 in PCT/EP10/61528 Filed Aug. 8, 2010.

* cited by examiner

1 = plasma jet
2 = High-voltage electrode
3 = Grounded electrode
4 = Dielectric
5 = Process gas
6 = Active substance feed 1 = Plasma jet
2 = Outer electrode
3 = Outer electrode (grounded)
4 = Inner electrode
6 = Process gas (Gas feed)
7 = Active substance feed
8 = Gas channel (= gas mixing device = transporter)
9 = Cells to be treated
10 = Gas jet
11 = Isolation
12 = Power supply unit

ATMOSPHEREIC PRESSURE PLASMA JET FOR DELIVERING ACTIVE SUBSTANCES ENCAPSULATED IN NANOPARTICLES OR MICROPARTICLES TO TISSUE

BACKGROUND OF THE INVENTION

Field of the Invention

The invention relates to a method and apparatuses for treatment of living tissue by means of a plasma (plasma operation). The apparatus contains not only conventional devices for plasma production and production of a field, for example by means of electroporation, but also devices for mixing and transport of active substances, encapsulated in nanoparticles and microparticles.

1. Problem of Cancer Therapy:

DISCUSSION OF THE BACKGROUND

At present, the standard methods of cancer therapy, used individually or in combination, are operation, chemotherapy and radiation therapy. Currently, a method called "electroporation therapy" (EPT), "electrochemotherapy" (ECT) or "high-voltage impulse therapy" (HVIT) is undergoing clinical trials, which method is based on the fact that the membrane pores of the cancer cells are selectively and reversibly opened, for a short period of time, by means of the targeted use of pulsed electrical fields (—electroporation), so that a drastically increased uptake of the active substances used for chemotherapy, such a bleomycin or cisplatin, for example, by the cells is achieved. The advantages as compared with conventional chemotherapy consist in that in the case of electrochemotherapy, the required active substance dose can be selected to be about twenty times lower, and that because of the selective destruction, an effect that is gentle on the tissue is achieved, with minimal scar formation, along with a great reduction in the side effects caused by the chemotherapy drug. Because the cancer cells differ from the healthy cells in terms of their size, the structure of the cell membrane, and the electrical properties, selectivity of electroporation can be achieved by means of a suitable selection of the amplitude, number, duration and frequency of the high-voltage impulses. Various apparatuses for this are described in DE69604509, DE69928383 and DE60106901, for implementing such controlled, selective electroporation of cells.

Even though the active substance dose can be significantly reduced in electrochemotherapy, it is not possible to do completely without the use of expensive chemotherapy drugs, which have side effects on healthy body tissue, although to a lesser degree than in the case of conventional chemotherapy.

2. Problem of Healing of Chronic Wounds:

Because chronic wounds are generally the consequence of underlying diseases, the primary approach to healing them consists in diagnosis and causal therapy of this underlying illness. In many cases, however, healing of the underlying disease is not possible, so that attempts are made to achieve healing of the wound despite the continuing underlying disease, by means of different types of local therapy measures, for example surgical procedures, wound cleaning and disinfection, the use of antibiotics and of special wound dressings and wound bandages.

The constantly increasing supply of therapeutic products (ointments, tinctures, powders, antiseptics, antibiotics) as well as bandage materials and bandage material systems for the treatment of chronic wounds, and the related problem of correct selection and use, leads to a therapeutic method of procedure that is characterized by a large number of different, uncoordinated and often ineffective medical measures (—polypragmasia), and this is often the cause for delays in healing and increases in cost.

3. Problem in the Topical Application of Active Substances to the Skin:

The skin is not only the largest organ of our organism, it also represents the barrier of our body with regard to the environment. It prevents the loss of water and the entry of environmental toxins into our skin. This barrier function represents a great problem in the topical application of active substances, i.e. of substances that are applied to the skin and that are supposed to have an effect in the region of the living cells. For this purpose, it is necessary that these substances penetrate the stratum corneum.

Many different methods were developed to stimulate this process. These include the use of different formulations that support the penetration of topically applied substances. These include micro-emulsions and liposomes. Aside from exerting an influence by way of the formulation, there is also a great number of methods that artificially damage the barrier in order to allow improved penetration of active substances. These include iontophoresis as well as the use of micro-needles that produce small holes having a depth of approximately 100-200 µm in the skin, and thereby allow improved penetration. Furthermore, different types of occlusions are also used to bring topically applied substances into the region of the living cells.

SUMMARY OF THE INVENTION

The task of the invention consisted in eliminating the disadvantages of the solutions described in the state of the art.

This and other objects have been achieved by the present invention the first embodiment of which includes an apparatus for treatment of living cells by plasmaporation, comprising a device for production of a plasma; and a device for mixing and transport of an active substance.

DETAILED DESCRIPTION OF THE INVENTION

Figure 1:
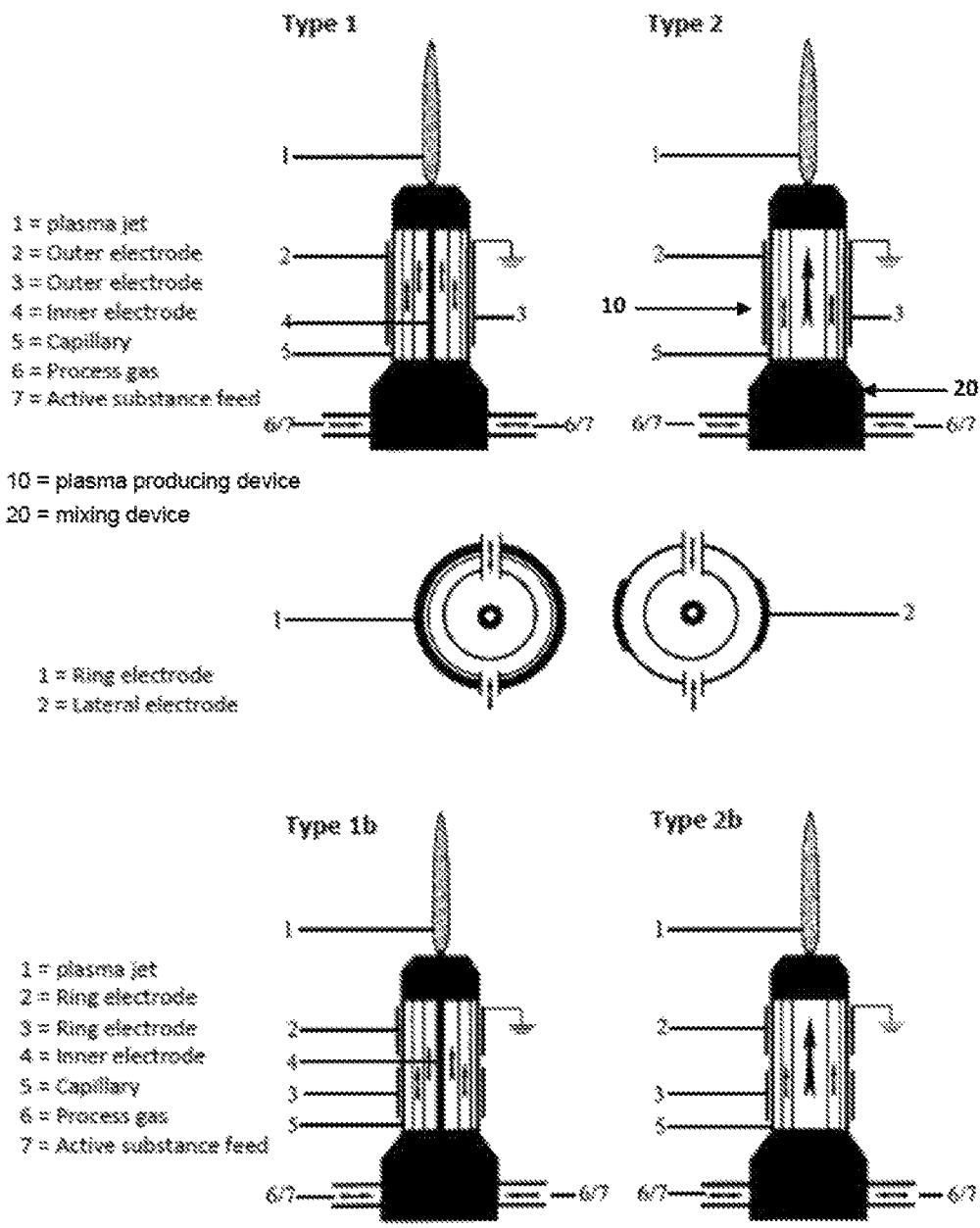
FIG. 1 shows a structure of the apparatus according to the invention.

The invention is based on the idea of allowing substances to act on living cells by means of a plasma. Within the scope of studies concerning the use of a plasma jet for treatment of the skin surface, for disinfection, it was found that topically applied dyes can penetrate the barrier of the skin very effectively and quickly during plasma treatment. This is possible not only if these topically applied substances are applied before the plasma treatment, but also if they are applied after the plasma treatment.

Surprisingly, the interaction between plasma and tissue results in a change in the composition of the lipid structures, so that a "door" virtually opens for a short time, which allows entry of the topically applied substances into the region of the living cells. How long this "door" remains open depends on the energy introduced and the temperature of the plasma. Under advantageous conditions, it is even possible to apply the topically applied substances to the skin after the plasma treatment and to nevertheless achieve efficient and effective penetration in the region of the living cells. After this time window, the lipid cells return to their original form in the region of the stratum corneum, and further penetration of topically applied substances is then no longer possible. This has the advantage, at the same time, that only the topically applied substances used in targeted manner penetrate the barrier, but long-term opening of the barrier does not occur, so that viruses, bacteria and environmental toxins cannot use this entry portal to get into the region of the living cells.

Studies with in vivo laser scanning microscopy have confirmed this process. It was possible to clearly show that without plasma treatment, a fluorescence-marked formulation that was applied topically could be detected only in the region of the skin surface or in the upper layers of the stratum corneum. After plasma treatment, it was possible to detect this formulation also in the region of the living cells, at high concentration.

On the basis of this invention, it is possible to solve the following problems:
1. Problems in cancer therapy: local, selective destruction of cancer cells, application of active substances, e.g. of chemotherapy drugs, at a low dose
2. Problem of the healing of chronic wounds: new therapeutic approach for improving wound treatment as a combination of an antiseptic effect with stimulation of the new formation of healthy tissue and by means of targeted application of active substances
3. Problem in the topical application of active substances to the skin: penetration of the upper layers of the stratum corneum.

Surprisingly, it has been possible to introduce substances into the skin in such a manner that they are not destroyed or converted during the plasma discharge. In this connection, a decisive solution approach is the stabilization of chemical substances with regard to the electrical discharge (in this connection, various chemical methods are possible), for example encapsulation of the active substances in nanoparticles or microparticles that possess a sheath that is not destroyed by the plasma discharge. These nanoparticles or microparticles are passed into the skin, the sheath dissolves there (in the region of the living cells), and the active substance is released.

In the case of treatment of the cells of chronic wounds, effective antiseptic action of the plasma can be achieved by means of the parallel use of electroporation and atmospheric pressure plasma, with an optimal selection of the treatment parameters, with simultaneous stimulation of the new formation of healthy tissue cells.

At the same time, sterilization is achieved in that the cell membrane pores of the microorganisms to be killed are temporarily opened by means of reversible electroporation with simultaneous plasma action, and thereby more effective destruction of the cells by means of the radicals produced in the plasma can take place.

In the case of use for cancer therapy, a significant reduction in treatment costs is achieved by means of the reduction in the dose of expensive chemotherapy drugs.

In the treatment of chronic wounds, the advantage of the invention consists in the possibility of getting from a polypragmatic treatment to an efficient and more cost-advantageous, universally usable treatment by means of which effective antiseptic action is achieved, which is connected with stimulation of new formation of healthy tissue.

By means of the additional use of electroporation during sterilization, decontamination or treatment of medical products by means of atmospheric pressure plasmas, a significant improvement in sterilization efficiency is achieved.

The apparatus according to the invention, for treatment of living cells by means of a plasma, is characterized in that it contains not only conventional devices for plasma production and production of an electrical field, preferably by means of electroporation, but also devices for mixing and transport of active substances encapsulated in nanoparticles and microparticles, for introduction into cells and tissue. The plasma is preferably a normal-pressure plasma, particularly a cold or non-thermal atmospheric-pressure plasma. The apparatus according to the invention comprises at least one electrode, at least one gas feed, at least one gas mixing device or mixing device of gases with microparticles and nanoparticles, and at least one voltage supply. In addition, the apparatus possesses a gas jet, at least one dielectric, insulation, and at least one electrode (low voltage to high voltage), as well as at least one gas channel for mixing or for transport of active substances in the gas stream.

The method according to the invention comprises the following steps, where these steps can take place one after the other or at the same time:
  Mixing of gases with active substances encapsulated in microparticles and nanoparticles
  Generation of a plasma
  If necessary, production of an electrical field, preferably by means of electroporation
  Application of the active substances by means of the plasma and, if applicable, of the electrical field below the upper layers of the stratum corneum of the skin The active substances can be stabilized with regard to the electrical discharge, preferably by means of encapsulation (functional surface).

Use of the apparatus described and/or of the method, according to the invention, consists in the introduction and application of active substances into cells (plasmaporation) or to the surface of objects, wounds, skin, plant and animal products, as well as tissue, characterized in that a reversible influence is exerted on the outer cell structures, by means of the plasma conditions, which influence allows or supports the introduction or application of active substances and active particles.

A method for treatment of skin diseases, cancer diseases, chronic wounds, for supporting postoperative wound healing, diseases of the gums (e.g. periodontitis) and of bone healing, characterized in that the plasma additionally transports active substances in the gas stream of the discharge is also an object of the present invention.

Another object of the present invention is a method for introduction of active substances into cells, to influence the metabolism of the cells, where the cells are selectively opened for the introduction of active substances (chemical substances) by means of plasmaporation.

The present invention is a combination of known elements (parallel use of electroporation and plasma) and new elements (transport of active substances in the gas stream, for treatment of cells).

With the invention being presented, the treatment of living cells by means of a cold, non-thermal atmospheric-pressure plasma with simultaneous electroporation of the cells and simultaneous or nearly simultaneous introduction of active substances encapsulated in microparticles and nanoparticles for influencing the metabolism of the cells is made possible for the first time. The active substance is applied to the skin with the gas stream of the plasma jet and is transported onto the region of the living cells through the barrier that has been opened by the plasma. After the end of the plasma-tissue contact, the barrier is closed again immediately. Intact structures that prevent penetration of bacteria, viruses and fungi into the region of the living skin are formed.

Figure 2:
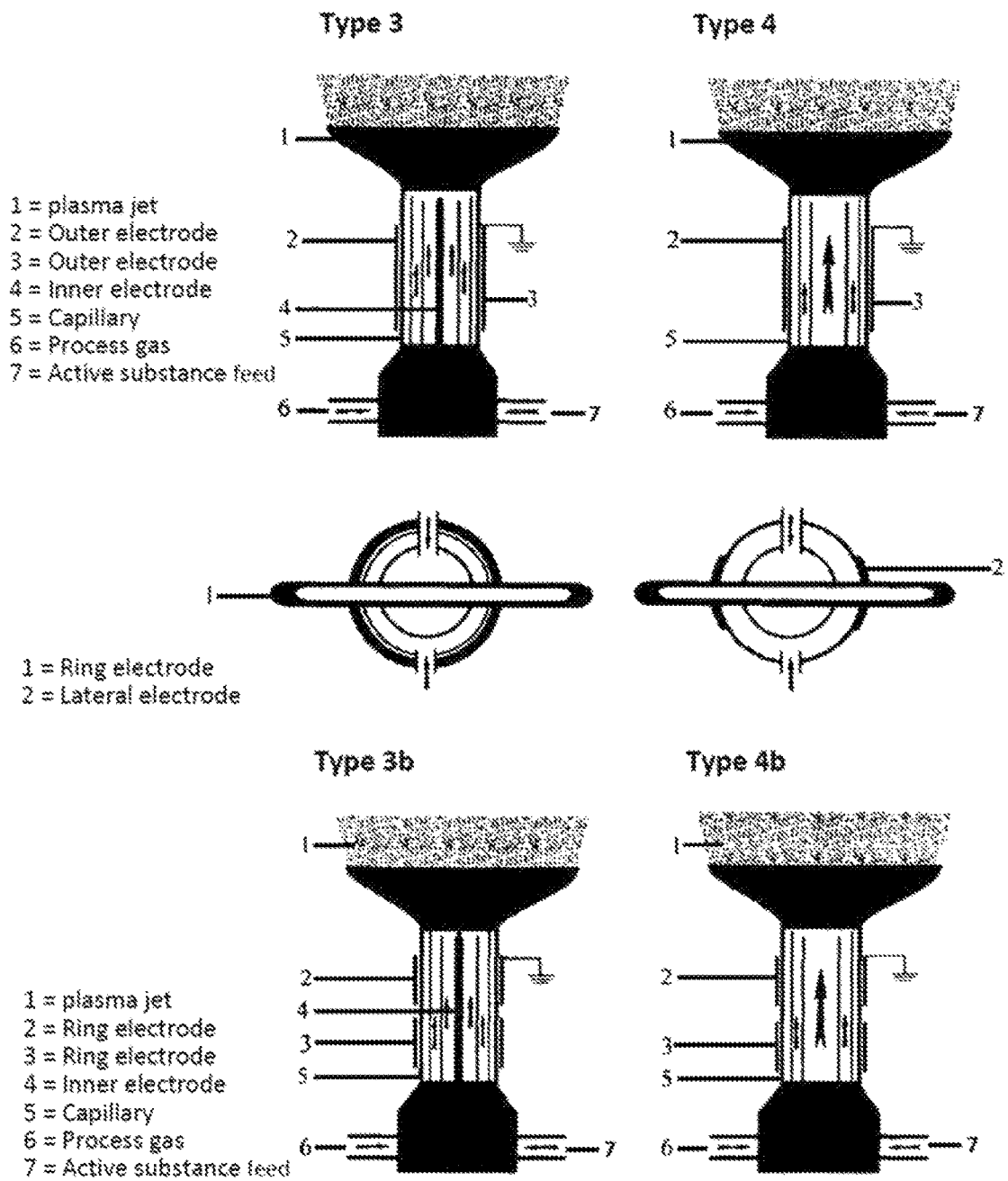
FIG. 2 shows a structure of the apparatus according to the invention.
Figure 3:
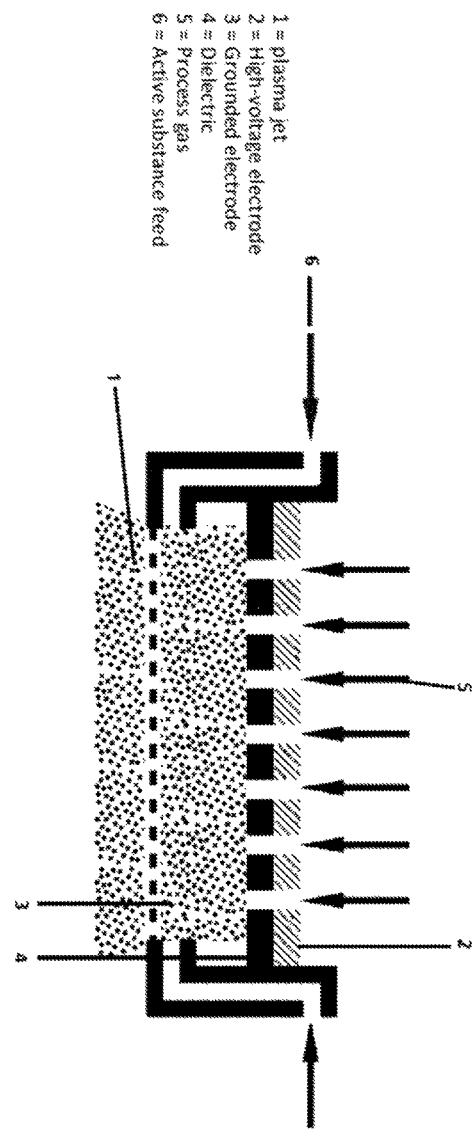
FIG. 3 shows a structure of the apparatus according to the invention.
Figure 4:
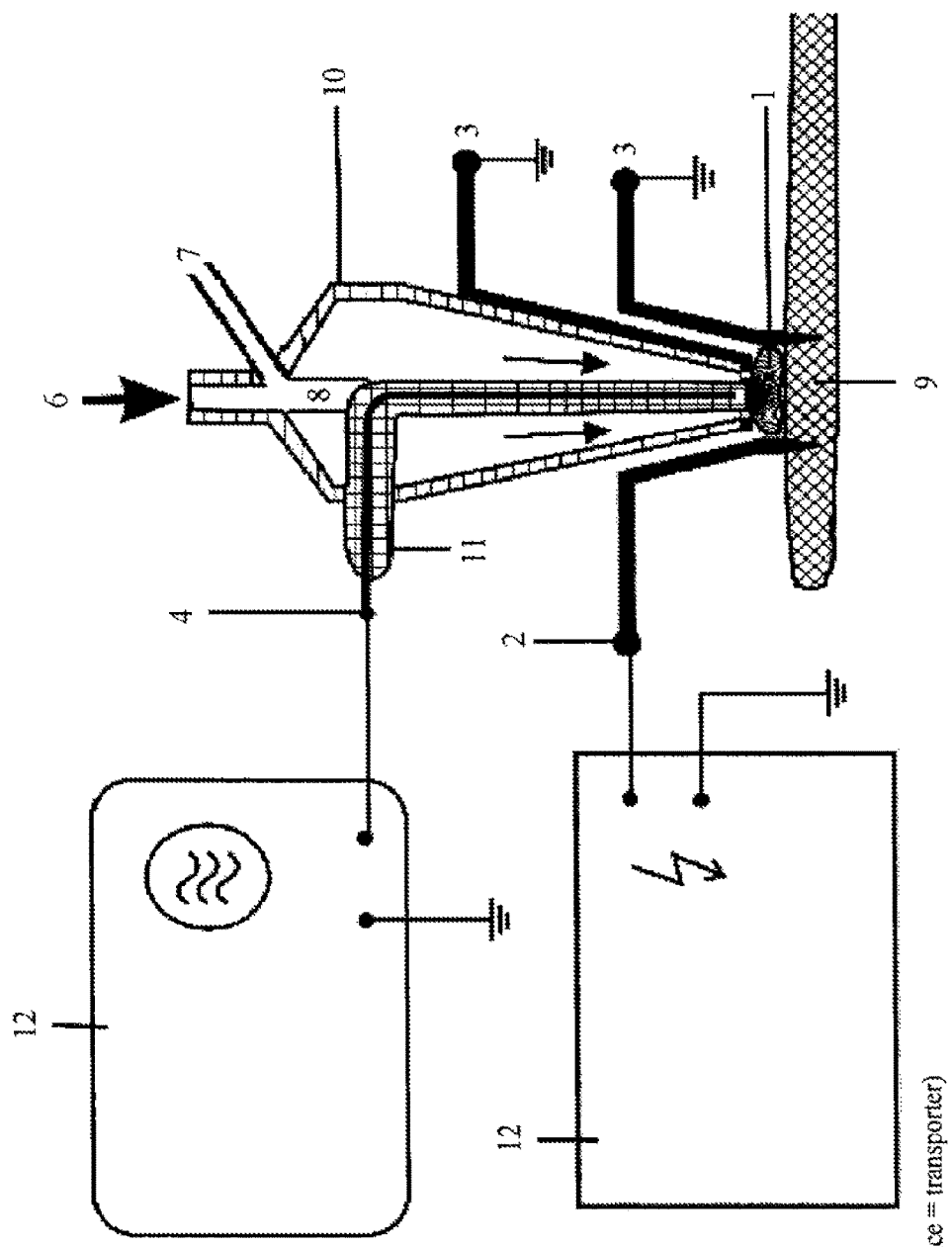
FIG. 4 shows a structure of the apparatus according to the invention.

The invention will be explained in greater detail using drawings, without being restricted to these drawings. FIG. 1 to FIG. 4 show the fundamental structure of the apparatus according to the invention.

The invention claimed is:

1. An apparatus for treating a living tissue by exposing the living tissue to an atmospheric-pressure plasma jet that contains an active substance, the apparatus comprising:

(i) a plasma producing device configured for producing the atmospheric-pressure plasma jet, said plasma producing device comprising at least one electrode and at least one voltage supply for generating as plasma discharge;

(ii) a feed of the active substance encapsulated in nanoparticles or microparticles, where said nanoparticles or microparticles possess a sheath;

(iii) a mixing device configured for mixing said feed of active substance with a gas stream and for transporting the active substance in said gas stream;

wherein said sheath is made from a material that (a) is not destroyed by the plasma discharge produced in said plasma producing device and (b) dissolves to release said active substance once the nanoparticles or microparticles are introduced into said living tissue.

2. The apparatus of claim 1, wherein the active substance is encapsulated in the nanoparticles.

3. The apparatus of claim 1, wherein the active substance is encapsulated in the microparticles.

4. The apparatus of claim 1, wherein the active substance is at least one chemotherapy drug.

5. The apparatus of claim 1, wherein the active substance is at least one anticancer drug.

6. The apparatus of claim 1, wherein the active substance is at least one for treating a wound or to support post-operative wound healing.

7. The apparatus of claim 1, wherein the active substance is at least one for promoting the growth of healthy tissue.

8. The apparatus of claim 1, wherein the active substance is at least one for treating a gum or bone disease.

9. The apparatus of claim 1, wherein the atmospheric-pressure plasma jet is of a cold or not atmospheric-pressure plasma.

10. The apparatus of claim 1, wherein the mixing device comprises at least one gas channel.

* * * * *